United States Patent
Pankow

[19]

[11] Patent Number: 6,134,736
[45] Date of Patent: *Oct. 24, 2000

[54] CONTACT LENS TREATMENT APPARATUS

[75] Inventor: Mark L. Pankow, Chicago, Ill.

[73] Assignee: IsoCLEAR, Inc., Ill.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/236,734

[22] Filed: Jan. 25, 1999

Related U.S. Application Data

[60] Continuation of application No. 08/763,857, Dec. 11, 1996, Pat. No. 5,891,258, which is a division of application No. 08/398,057, Mar. 2, 1995, Pat. No. 5,657,506, which is a continuation of application No. 08/004,961, Jan. 15, 1993, abandoned.

[51] Int. Cl.[7] .......................... G02C 13/00; B08B 11/00
[52] U.S. Cl. .................................. 15/104.92; 15/104.93; 15/214; 15/244.1; 206/5.1
[58] Field of Search .................... 134/6, 40, 42, 134/901; 514/839, 840; 15/104.92, 104.93, 104.94, 208, 209.1, 214, 244.1, 244.3, 244.4; 206/5.1

[56] References Cited

U.S. PATENT DOCUMENTS

| | | | |
|---|---|---|---|
| 1,003,761 | 9/1911 | Lehmann | 15/214 |
| 1,708,728 | 4/1929 | Kilbride | 15/214 |
| 2,906,643 | 9/1959 | Dennis | 15/244.4 |
| 2,932,383 | 4/1960 | Fagan | 206/5 |
| 2,967,607 | 1/1961 | Llollinger | 206/5.1 |

(List continued on next page.)

FOREIGN PATENT DOCUMENTS

| | | |
|---|---|---|
| 268087 | 1/1986 | European Pat. Off. . |
| 2061709 | 5/1981 | United Kingdom . |
| 9008604 | 8/1990 | WIPO . |

OTHER PUBLICATIONS

Pall BioSupport Division, Procedure for Blocking Non–Bio-specific Binding Sites on Pall BioSupport Membranes, Jan. 1988.
Pall BioSupport Division, Fluorotrans PVDF Membrane.
Pall Ultrafine Filtration Company BioSupport Group, Membranes Proven in the Lab and Engineered for the Market, 1992.
Pall BioSupport Corporation, Immunodyne Immunoaffinity Membrane.
Pall BioSupport Corporation, Biodyne Nylon Membranes.
Pall BioSupport Corporation, Pall Membra–Pad Membrane Dipsticks.

(List continued on next page.)

*Primary Examiner*—Jeffrey Snay
*Attorney, Agent, or Firm*—Cook, Alex, McFarron, Manzo, Cummings & Mehler

[57] ABSTRACT

A self-contained single-use apparatus for cleaning and hydrating a pair of contact lenses comprises a housing including a pair of hollow snap-lock lens containers in which opposed layers of a deformable relatively hydrophobic reactive material having surfaces arranged for non-abrasive contiguous wetted contact with the optical surfaces of the lenses when the lenses are enclosed in the housings. While in contact with the optical surfaces contaminants in the lenses are attracted to the contacting surfaces of the reactive layers. Upon removal of the lenses the attracted contaminants remain on the contacting surfaces and are disposed of with the housing. The container contains sufficient absorbed liquid for maintaining the lens in a hydrated condition while being treated in the container during the treatment process.

18 Claims, 3 Drawing Sheets

U.S. PATENT DOCUMENTS

| | | | |
|---|---|---|---|
| 3,037,616 | 6/1962 | Phipps, III | 206/5 |
| 3,054,412 | 9/1962 | Nickell | 134/137 |
| 3,083,819 | 4/1963 | Entzminger | 206/5 |
| 3,085,584 | 4/1963 | Hollinger . | |
| 3,149,364 | 9/1964 | Stalcup | 134/156 |
| 3,344,461 | 10/1967 | Baptist et al. | 15/506 |
| 3,369,656 | 2/1968 | Floor | 206/5.1 |
| 3,377,643 | 4/1968 | Skinner | 206/56 |
| 3,808,118 | 4/1974 | Golias . | |
| 3,871,395 | 3/1975 | Murry | 134/107 |
| 3,977,517 | 8/1976 | Kadlecik et al. | 206/5.1 |
| 3,990,579 | 11/1976 | Manning | 206/5.1 |
| 3,998,590 | 12/1976 | Glorieux . | |
| 4,187,574 | 2/1980 | Wrue | 15/104.92 |
| 4,202,740 | 5/1980 | Stoner et al. | 205/701 |
| 4,493,783 | 1/1985 | Su et al. | 510/113 |
| 4,533,399 | 8/1985 | Mencke | 134/6 |
| 4,559,662 | 12/1985 | Kunold, Jr. | 15/104.94 |
| 4,613,379 | 9/1986 | Su et al. | 134/7 |
| 4,693,985 | 9/1987 | Degen et al. . | |
| 4,732,185 | 3/1988 | Cowle et al. | 204/267 |
| 4,792,414 | 12/1988 | Su et al. . | |
| 4,839,082 | 6/1989 | Bhaita . | |
| 4,840,681 | 6/1989 | Pompe . | |
| 4,852,592 | 8/1989 | DiGangi et al. . | |
| 4,872,965 | 10/1989 | Pankow . | |
| 5,017,238 | 5/1991 | Chromecek et al. . | |
| 5,037,484 | 8/1991 | Su et al. . | |
| 5,037,485 | 8/1991 | Chromecek et al. . | |
| 5,054,610 | 10/1991 | Ajello . | |
| 5,071,276 | 12/1991 | Nielson et al. . | |
| 5,073,202 | 12/1991 | Wallach . | |
| 5,100,477 | 3/1992 | Chromecek et al. . | |
| 5,114,686 | 5/1992 | Tanaka et al. . | |
| 5,128,058 | 7/1992 | Ishii et al. . | |
| 5,227,039 | 7/1993 | Pankow . | |
| 5,368,708 | 11/1994 | Pankow . | |
| 5,439,572 | 8/1995 | Pankow . | |
| 5,529,678 | 6/1996 | Pankow . | |

OTHER PUBLICATIONS

Millipore Corporation, Protein (Western) Blotting Applications of Immobilon PVDF Transfer Membrane:Transfer of Protein Resolved in a High Resolution Two Dimension Gel System, Feb. 1987.

Millipore Corporation, Basic Technique for Use of Immobilon PVDF Transfer Membrane in Protein (Western) Blotting Application from a Sodium Dodecyl Sulfate Polyacrylamide Gel Electrophoresis (SDS–PAGE) System, Feb. 1987.

Millipore Corporation, General Protein Staining for Protein (Western) Blotting Applications Using Immobilon PVDF Transfer Membranes, Feb. 1987.

Millipore Corporation, Protein (Western) Blotting Applications of Immobilon PVDF Transfer Membrane:Transfer of High Molecular Weight of Proteins from a Non–Denaturing Gel System, Feb. 1987.

Millipore Corporation, Protein (Western) Blotting Applications of Immobilon PVDF Transfer Membrane: Transfer of Basic Proteins From an Acid/Urea gel System at Acidic pH, Feb. 1987.

Millipore Corporation, The Use of the Immobilon–P (PVDF) Transfer Membrane for Alkaline DNA Transfer, Feb. 1987.

Millipore Corporation, Direct Protein Microsequencing From the Immobilon–P Transfer Membrane, Feb. 1987.

Millipore Corporation, Immobilon–P Transfer Membranes, Feb. 1988.

Millipore Corporation, Clinical Diagnostics Membrane Characterization Guide, Apr. 1989.

Cuno Life Science Division of Commercial Intertech Corp., Zetaffinity Media–Advanced Affinity Chromatography Supports, 1989.

Cuno Life Sciences Division of Commercial Intertech Corp. Zeta Plus Depth Media Clarification and Capillary Absorption, 1989.

W.L. Gore & Associates, Inc., PTFE vs PVDF, Jun. 8, 1991.

Lloyd, Material Sciences of Synthetic Membranes, pp. 1–21, 47–51, 63–70, 102–107, 115, 131–162, 165–195, 197–198, 237–243, 1985, ACS Symposium Series.

Kesting, Synthetic Polymeric Membranes–A Structural Perspective, pp. 15–17, 122–130, 158–159, 172–177, 186–192, 200–207, 230–235, 329–333, 1985, John Wiley & Sons.

Meltzer, Filtration in the Pharmaceutical Industry, Chapters 2 (pp. 61–86), 5 (pp. 299–365), Marcel Dekker, Inc.

Hou et al., Capture of Latex Beads, Bacteria, Endotoxin, and Viruses by Change–Modified Filters, vol. 40, No. 5, Applied and Environment Microbiology, Nov. 1980, pp. 892–896.

Berg et al., Interaction of a Group of Low Molecular Weight Organic Acids With Insoluble Polyamides I, vol. 54, No. 1, Journal of Pharmeceutical Sciences, pp. 79–84, Jan. 1965.

Renner, Immunoblotting and Dot Immunobinding, vol. 112, Arch Pathol Lab Med, pp. 780–786, Aug. 1988.

Cuatrecasas et al., Adsorbents for Affinity Chromatography, Use of N–Hydroxysuccinimide Esters of Agarose, vol. 11, No. 12, Biochemistry, pp. 2291–2299, 1972.

Cuatrecasas, Protein Purification by Affinity Chromatography, Derivatizations of Agarose and Polyacrylamide Beads, The Journal of Biochemistry, pp. 3059–3065, Jun. 25, 1970.

Callaghan et al., Affinity Blotting: Polyvinylifluoride (PVDF) is Superior to Nitrocellulose, p. 1377, Clinical Chemistry, vol. 36, No. 7, 1990.

Miller et al., Interfacial Phenomena–Equilibrium and Dynamic Effects, pp. 58–60, 93–95, 98–100 & 112–113, Marcel Dekker, Inc.

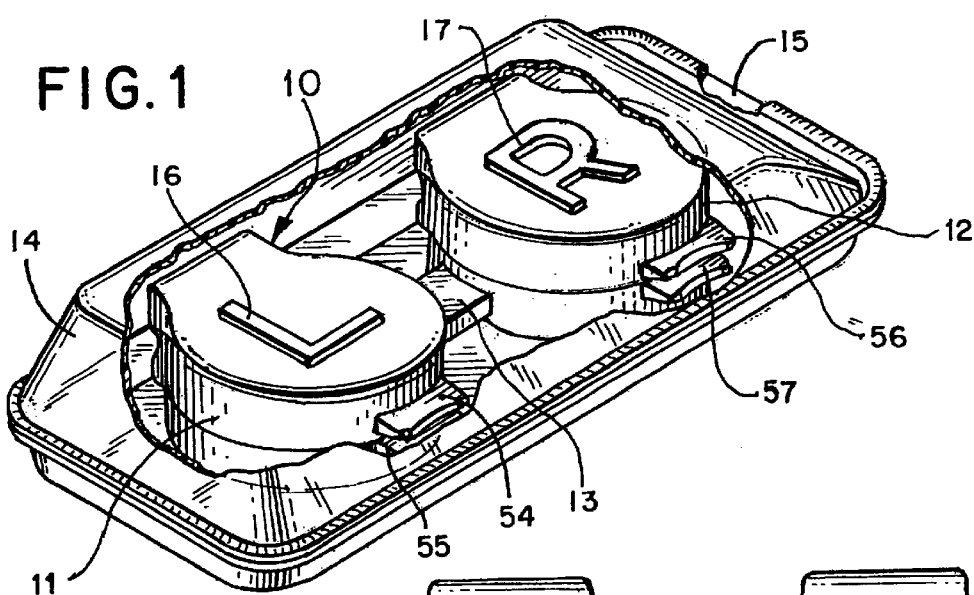
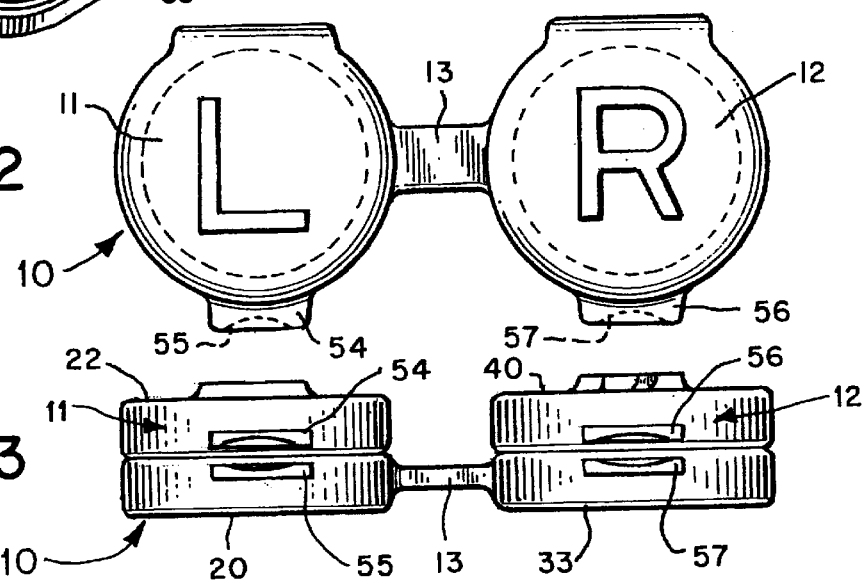
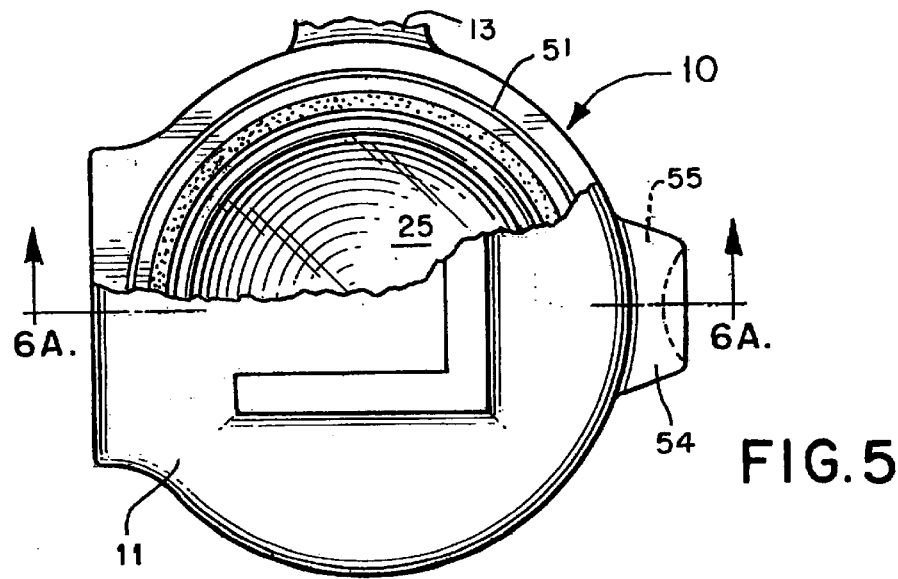

CONTACT LENS TREATMENT APPARATUS

This application is a continuation of application Ser. No. 763,857, filed Dec. 11, 1996, now U.S. Pat. No. 5,891,258, which is a divisional application of application Ser. No. 08/398,057, filed Mar. 2, 1995, now U.S. Pat. No. 5,657,506, which is a FWC continuation of Ser. No. 08/004,961, filed on Jan. 15, 1993, now abandoned.

BACKGROUND OF THE INVENTION

The present invention is directed to an apparatus and method for treating contact lenses. More particularly, the invention is directed to a stand-alone apparatus and method by which contact lenses can be cleaned and hydrated without the application of heat, mechanical agitation or cleaning chemicals to the lenses. In a particularly advantageous form the apparatus is single-use and disposable, and comprises a housing including a pair of closable liquid sealed lens containers within which the lenses are contained and brought into contiguous wetted contact with layers of reactive material during the treatment process.

Contact lenses have come into wide use for correcting a wide range of vision deficiencies or cosmetic use. Typically, such lenses are formed from a thin transparent plastic material shaped and dimensioned to fit over the cornea of the eye. The lenses include a concave interior first optical surface for contact with the eye, and an opposed and optically associated convex exterior second optical surface. The two surfaces together define a corrective lens medically prescribed for a particular eye.

Depending on the plastic material used to construct the lenses, the lenses may be either "hard" or "soft". Hard contact lenses, which are comparatively more rigid, are typically formed from a relatively hydrophobic material such as polymethylmethacrylate (PMMA). Soft contact lenses, which are comparatively more pliant, are typically formed from a relatively hydrophylic polymer such as hydroyethylmethacrylate (HEMA), which has the property of being able to absorb and bind a proportionately large amount of water within the polymer network. Soft contact lenses formed from such hydrophilic polymers, when hydrated, are more comfortable to wear than hard lenses because they better conform to the cornea of the eye and cause less irritation when worn for extended periods. For this reason, the great majority of contact lenses presently being prescribed are of the soft type.

Unfortunately, soft contact lenses while being worn may collect contaminants from the eye and its environment. These contaminants, for example, may include proteins and lipids from the tear fluid of the eye, and foreign substances such as cosmetics, soaps, airborne chemicals, dust and other particulate matter. Unless periodically removed, these contaminants may cause abrasion to the surface of the lens, may impair the visual acuity of the lens, and may serve as a nutrient media for potentially harmful microorganisms.

Furthermore, for wearing comfort it is necessary that soft contact lenses be maintained uniformly wetted at all times. While on the eye, the moisture content of the hydrophilic material of the lenses is maintained by tear fluid. However, when the lenses are removed for an extended period, as for cleaning or while sleeping, the lenses may dry out and become irreversibly damaged unless they are externally hydrated.

Consequently, various apparatus and methods have been developed for cleaning and hydrating soft contact lenses. For example, cleaning apparatus has been provided wherein the lenses are submersed in a variety of liquid cleaning agents, such as surficants, oxidants, disinfectants, enzymatic cleaners, or abrasives. Other cleaning apparatus has been provided which included mechanically operated or electrically powered components for vibrating, rotating, abrading, scrubbing, heating, agitating, subjecting to ultrasonic energy, or otherwise mechanically manipulating the lenses to enhance the cleaning action of the cleaning agent.

Such prior apparatus and methods have not been entirely satisfactory for various reasons, including lack of cleaning effectiveness with respect to certain of the various contaminants found on the lenses, undesirable complexity, excessive time required for use, and dependence on an external power source.

Furthermore, certain prior lens cleaning apparatus and methods required added post-cleaning lens treatment procedures such as rinsing before the lenses could be returned to the eye. Also, such apparatus and methods did not provide a convenient and effective means by which contaminants dislodged during cleaning could be retained for subsequent disposal. Unless a separate and time-consuming cleaning of the apparatus was performed, the dislodged, and possibly infectious contaminants could come into contact with the fingers of the user, and possibly the previously cleaned lenses.

Certain of the prior apparatus and methods such as those involving the application of heat (as during the boiling of the lenses) or those utilizing harsh chemical cleaning agents, actually exacerbated the contamination problem by denaturing the organic components of the contaminants, leaving an intractable layer of contamination. The accretion of such intractable layers over time resulted in increased irritation and decreased visual acuity, and ultimately in premature replacement of the lenses.

Moreover, those prior cleaning apparatus and methods which involved the removal of contaminants by mechanical means had the potential of scratching or otherwise damaging the surfaces of the lenses. Surface scratches potentially weaken the lenses and provide a site at which deleterious organisms such as bacteria can flourish.

Preferably, during the cleaning process (typically overnight) the lenses are maintained in a wetted condition, ready for use when the cleaning process has been completed. Certain prior apparatus did not provide for such hydration, and it was necessary that the lenses be moved to a separate hydration chamber upon completion of the cleaning process. This was not only inconvenient and time consuming, but increased the risk of damage to the lenses from additional handling.

Thus, a demand exists for an apparatus and method by which contaminated contact lenses can be conveniently and effectively cleaned with minimum handling and without the application of exterior power.

Accordingly, it is a general object of the present invention to provide a new and improved system, apparatus and method for cleaning contaminated contact lenses.

It is a more specific object of the invention to provide an apparatus for cleaning contaminated contact lenses wherein the lenses are concurrently maintained in a hydrated state and cleaned.

It is a further object of the present invention to provide a disposable single-use apparatus for cleaning contaminated contact lenses having closable liquid-sealed container within which the lenses are contained while being cleaned.

It is a further object of the invention to provide a self contained apparatus for cleaning a contaminated contact lenses wherein the optical surfaces of the lenses are received in a wetted environment in contiguous contact with reactive layers which attract contaminants from the lenses without the application of external force.

It is a further object of the invention to provide a method of cleaning contaminated contact lenses wherein the optical surfaces of the lenses are concurrently brought into contiguous contact with reactive surfaces in a liquid environment to cause contaminants to migrate from the lenses to the reactive surfaces.

SUMMARY OF THE INVENTION

The invention is directed to an apparatus for cleaning a contact lens of the type having a pair of opposed optical surfaces and contaminated with contaminant matter, comprising a layer of reactive material defining a first non-abrasive reactive surface operative when in wetted contact with a first optical surface of the lens to attract contaminant matter from the lens, the reactive surface being wetted and shaped for generally contiguous engagement between the optical surface and the reactive surface whereby contaminants migrate from the lens to the reactive surface.

The invention is further directed to a method for cleaning a contact lens of the type having two optical surfaces and contaminated with contaminant material, comprising the steps of:

positioning at least one of the optical surfaces of the lens in contiguous engagement with a reactive surface adapted to attract the contaminants from the lens;

maintaining the surfaces in contiguous wetted contact; and removing the lens from the reactive surface for use.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a contact lens treatment apparatus constructed in accordance with the invention contained within a sealed foil package.

FIG. 2 is a top plan view of the contact lens treatment apparatus of FIG. 1 showing the left and right lens containers thereof.

FIG. 3 is a side elevational view of the contact lens treatment apparatus of FIG. 2.

FIG. 5 is an enlarged plan view of the left contact lens container of FIG. 4.

DESCRIPTION OF THE PREFERRED EMBODIMENT

Figure 4:
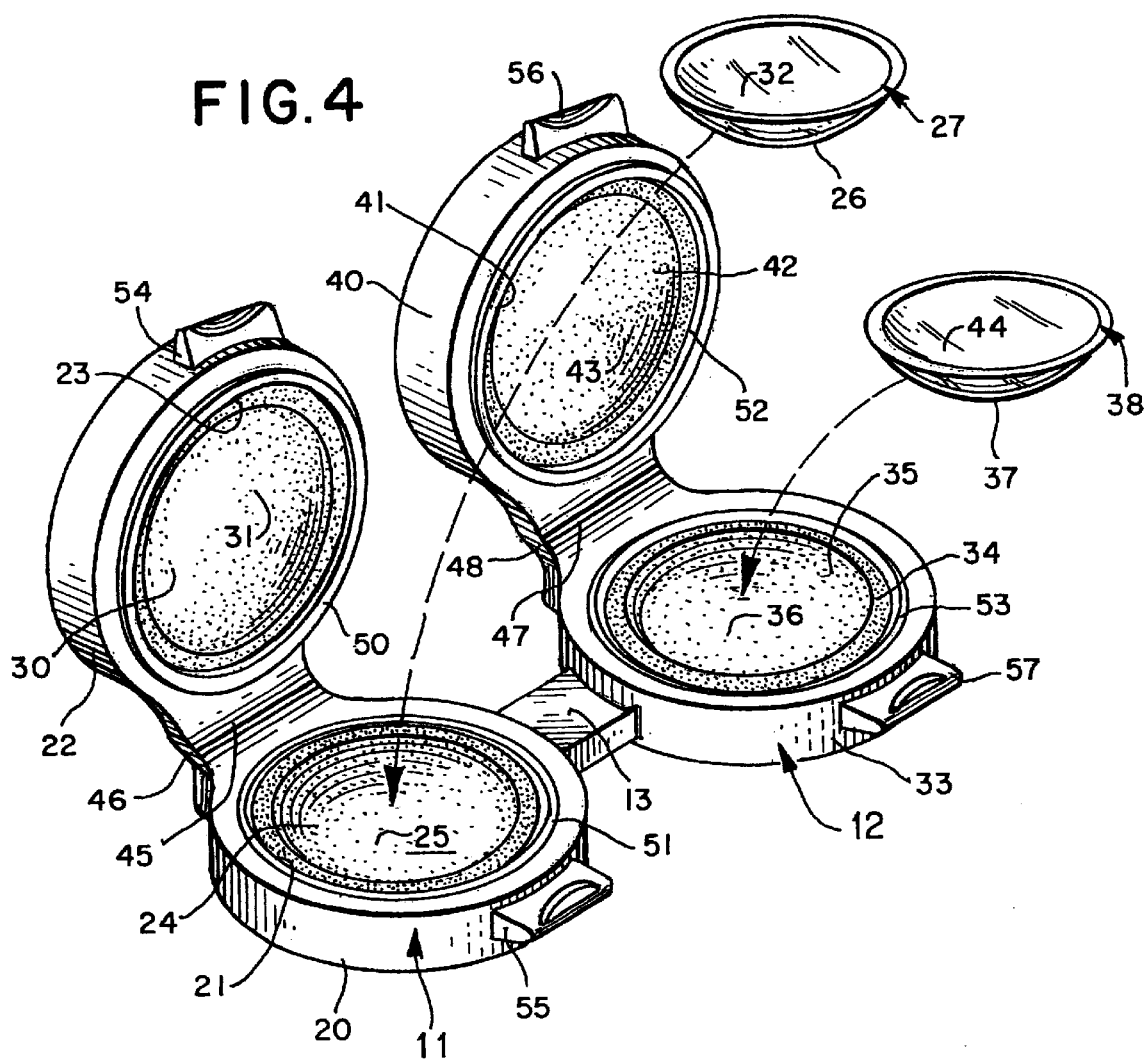
FIG. 4 is an enlarged perspective view of the contact lens treatment apparatus of FIGS. 1–3 showing the left and right lens containers thereof open for receiving a pair of conventional soft contact lenses for treatment.

Referring to the Figures, and particularly to FIGS. 1–3, a lens treatment apparatus 10 constructed in accordance with the invention is seen to include a single piece housing including a left lens container 11, a right lens container 12 and a bridge portion 13 extending between the two containers. The apparatus, which may be a disposable single-use apparatus, is preferably contained within a sealed package 14 formed of a foil or other liquid and gas impermeable material. A tab surface 15 or other means may be provided on the package to facilitate opening by a user. The apparatus 10 may include identification means such as a raised "L" 16 embossed on the cover of container 11 and a raised "R" 17 embossed on the top of container 12 to facilitate ready identification of the left and right lens containers by a user, even if vision-impaired.

As shown in FIGS. 4 and 6, the left lens container 11 includes a bottom section 20 defining a recess 21, and a top section 22 defining a recess 23. An insert 24 having a generally concave surface 25 is provided in the housing bottom portion 20 for engaging the convex optical surface 26 of a conventional soft left contact lens 27. An insert 30 having a generally convex surface 31 is provided in recess 23 for engaging the convex optical surface 32 of lens 27 when the housing is closed.

Similarly, the bottom section 33 of right lens container 12 defines a recess 34 in which an insert 35 having a generally concave surface 36 for receiving the convex optical surface 37 of a conventional soft right contact lens 38. The top section 40 of the right lens container defines a recess 41 in which an insert 42 having a generally convex surface 43 for engaging the concave optical surface 44 of lens 38.

The lower section 20 of the left lens container 11 is connected to the upper housing section 22 by a hinge portion 45 which includes a lateral portion 46 of reduced thickness (FIGS. 6A–6C) forming a living hinge along which the sections open as shown in FIG. 4. Similarly, the bottom right container section 33 is joined to the top right container section 40 by a hinge portion 47 having a living hinge portion 48.

A bulbous ridge 50 extending around the periphery of the top section 22 of the left lens container 11 engages a complementarily shaped and positioned channel 51 extending around the periphery of the bottom section 20 of the container to provide a liquid seal for containing liquid within the container. A similar ridge 52 and channel 53 liquid-seal the right lens container 12. A pair of tabs 54 and 55 are integrally formed on the top and bottom sections, respectively, of the left lens container 11 to facilitate opening and closing the container. Similarly, a pair of tabs 56 and 57 are integrally formed on the top and bottom sections, respectively, of the right lens container 12 to facilitate opening and closing that container.

The housing and integral lens containers are preferably formed of an inert semi-resilient plastic or other formable material such as by injection molding or other suitable manufacturing technique. Preferably, for minimum cost the containers and the connecting bridge member are formed as a single piece in a single forming operation. The plastic may be colored for optimum visibility or to indicate some particular characteristic of a particular assembly.

Figure 6A:
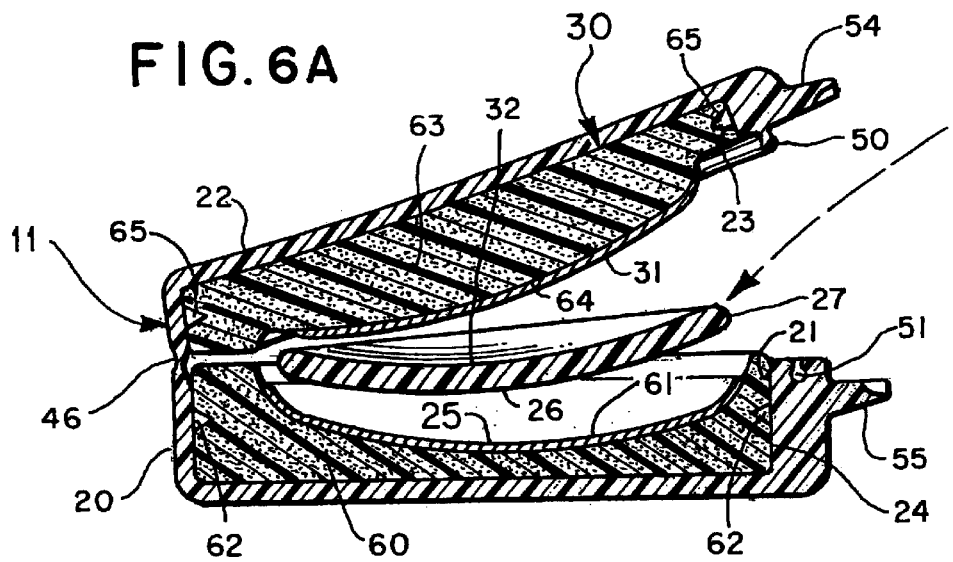
FIG. 6A is an enlarged cross-sectional view of the left lens container taken along line 6—6 of FIG. 5 showing the lens container open for receiving a conventional soft contact lens for treatment.
Figure 6B:
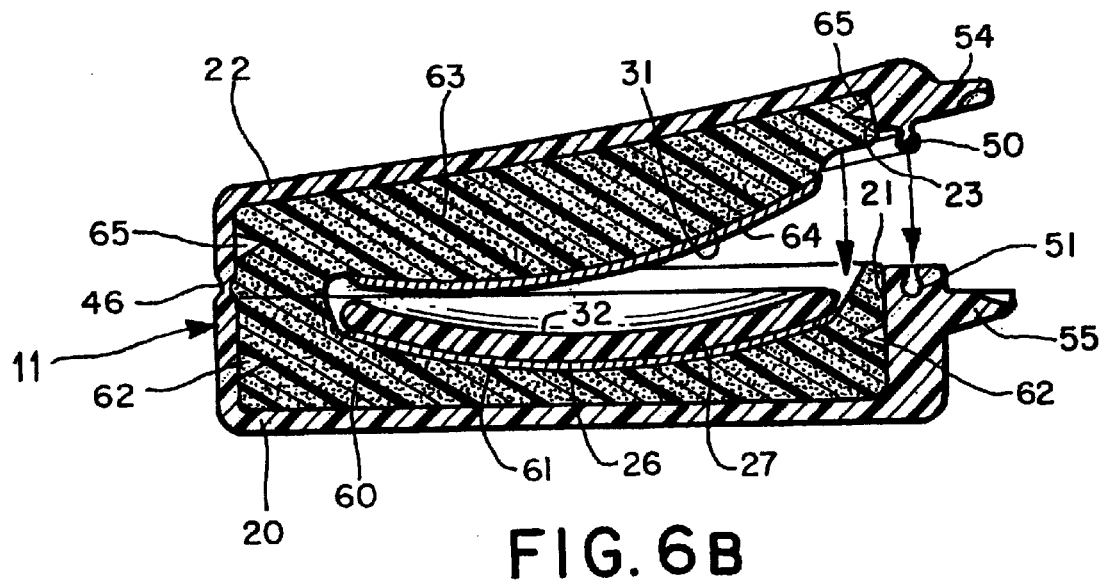
FIG. 6B is a cross-sectional view similar to FIG. 6A showing the lens seated in the container.
Figure 6C:
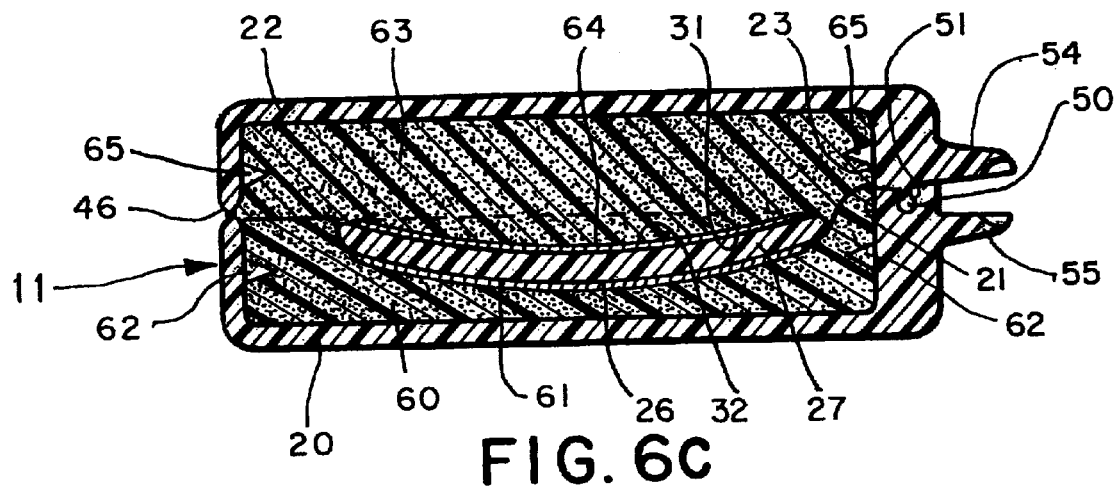
FIG. 6C is a cross-sectional view similar to FIGS. 6A and 6B showing the lens container closed with the lens positioned within for treatment.

Referring to FIGS. 6A–6C, insert 24 is seen to comprise a relatively thick porous and compressible sponge-like layer 60 dimensioned to fit snugly within recess 21 and formed with a generally concave surface over which a thin reactive layer 61 of a reactive material is provided to form the concave lens engaging surface 25. A plurality of spike-like tines 62 may be provided on the inside surface of recess 21 to assist in holding insert 24 in the recess. Similarly, insert 30 comprises a resilient porous sponge-like layer 63 dimensioned to fit snugly within recess 23 and shaped with a generally convex surface over which a thin reactive layer 64 of reactive material like that forming layer 61 is provided to form lens engaging surface 31. A plurality of spike-like tines 65 may be provided on the surface of recess 23 to assist in holding insert 30 in the recess.

As shown in FIG. 6C, when the left lens container 11 is closed reactive surface 25 is brought into contiguous engagement with optical reactive surface 26 and reactive surface 31 is brought into contiguous engagement with optical surface 32. The compressible sponge-like layers 60 and 63 are preferably dimensioned slightly oversize in their respective recesses, so that as the top and bottom sections of the lens container come together the layers are slightly compressed to provide a conforming contiguous contact between the optical surfaces 26 and 32 of the lens and the respective contacting surfaces 25 and 31 of the inserts.

During the manufacture of lens treatment apparatus 10 compressible layers 60 and 63 within the left lens housing 11 are preferably moistened with an ophthalmologically-compatible solution. When contact lens 27 is inserted in the housing for cleaning (as shown in FIG. 6A), and the container is subsequently closed by the user (as shown in FIGS. 6B and 6C), the accompanying compression of layers 60 and 63 causes solution absorbed therein to flow around the ends of reactive layers 61 and 64 (FIG. 6C) and around, over and under lens 27, providing a fluid layer between the optical surfaces 26 and 32 of the lens and the contiguous contacting surfaces 25 and 31 of reactive layers 61 and 64, respectively.

In accordance with the invention, reactive layers 61 and 64 may be formed from a surface reactive material which is hydrophobic relative to the relatively hydrophylic material of lens 27 and which has an average pore size slightly less than that of the protein contaminants of the lens. Consequently, when the optical surfaces of the lens are brought into wetted contiguous contact with the surface of these layers, lipids and other protein contaminants attached to the lens migrate from the surface to the surfaces of the reactive layers, and remain there when the lens is removed. This occurs on both the concave and convex optical surfaces of the lens, the contaminants being attracted to the adjacent reactive layers by reason of the natural migration of hydrophobic proteins and lipids and other contaminants from a less hydrophobic environment (the lens surface) to a more hydrophobic environment (the reactive layer surface) through the ophthalmologically-compatible solution.

For optimum migration the reactive layer must conform faithfully to the surface of the lens. To this end reactive layers 61 and 64 are preferably thin and flexible, and deformable by their associated sponge-like compressible layers 60 and 63 to the optical surfaces of the lens. The reactive layers 61 and 64 may be joined to their associated sponge-like layers by known techniques such as vapor deposition or spraying of the reactive material over the relatively more porous surface of the underlying compressible layer.

The right lens container 12, which is preferably identical in construction to the left lens container 11, includes inserts 35 and 42 formed of the same materials and having the same dimensions as inserts 24 and 30 of the left lens container 11.

It is preferable that lens housings 11 and 12 each have sufficient interior volume to enable an adequate volume of ophthalmologically-compatible solution to be absorbed in the compressible layers of each to maintain the lenes wetted during processing. Leakage and evaporation of the ophthalmologically-compatible solution from the lens containers is prevented prior to, during and after treatment of the lenses by ridge 50 and channel 51 in container 11, and identical structures in container 12, which extend around the entire periphery of the containers. When the containers are closed as shown in FIG. 6C, the ridges fit into the channel, forming both tight mechanical and tight fluid seals. These seals, and the seal provided by foil package 14, prevent evaporation of the ophthalmologically- compatible solution during even long term storage.

The compressible layers 60 and 63 are preferably formed from a highly porous absorbent material which accepts and retains moisture within its porous structure, and has an appreciable moisture content and therefore does not generally require re-wetting prior to use. Inert foraminous materials such as reticulated foams and papers are preferred materials for this purpose. Preferred ophthalmologically-compatible solutions for wetting the compressible layers include those known ophthalmologically-compatible solutions such as sold by Bausch & Lomb, Alcon, Giba-Geigy, and Allergan. The solutions may contain ophthalmologically-compatible anti-microbial agents or preservatives.

The reactive layer may be formed from a highly porous non-abrasive relatively polymeric material such as polytetrafluoroethylene (PTFE), polyvinylidene fluoride (PVDF), polypropylene, polyethylene, polyacrylonitrile, polymethylmethacrylate, polysulfone, polycarbonate, or cellulose acetate. PFTE is commercially available from W.L. Gore & Associates, Inc. PVDF is commercially available from the Millipore Corporation.

Polymers which exhibit a charged surface to which contaminants are attracted are suitable for use in the reactive layers, and include certain cellulosics, polyamides, and nylon-based compositions, such as those commercially available from the Pall Corporation.

Other suitable reactive materials are those that have been altered such chemical linkage occurs between the reactive material and reactive chemical groups found on proteins and other biological macromolecules contaminating the lens. The actual active group or groups that result in a covalent chemical linkage may depend on the pH of the surrounding fluid. "IMMUNODYNE", a product of the Pall Corporation is a commercially available example of one such material.

The attraction of lens contaminants to the reactive layer is the result of multiple forces and reactions which result in a greater net force being exerted between the reactive material and the contaminant than between the lens material and the contaminant. The forces include physicochemical forces, such as hydrophobic interactions at the molecular level which result from non-polar substances attracting other non-polar substances in the presence of more polar molecules such as water. Other molecular forces, such as Brownian motion or simple diffusion, and other attractive forces, such as London-van der Waals forces, may also contribute to the migration.

Furthermore, it has been found that those compositions that typically contaminate a lens are, after being drawn off the lens to the reactive material, adsorptively sequestered onto the reactive layer. The adsorptive sequestration of the contaminants may be due, in part, to the net electric charge of the contaminant and the opposite electric charge of the reactive material. The net charge varies with the type of contaminant and the composition and pH of the moisture or fluid that surrounds the contaminant.

The surface configuration of the reactive material may be varied in size and shape to optimize the performance of the reactive material and thereby the performance of the treatment apparatus. Material including pores of only a relatively large diameter advantageously is able to accommodate contaminants both of a large size and a wide range of smaller sizes. However, as the diameter of the pores increases, the pore surface area, and hence the adsorptive capacity of the material, decreases. Reactive material including pores having a wide range of diameters and including pores of smaller sizes will have a greater pore surface area and thereby greater adsorptive capacity (compared to a material having pores of only a larger diameter). To draw and retain the largest percentage of contaminants from a lens, the pore diameter of the reactive material preferably is within the range of approximately 0.1 micron to approximately 2 microns. A reactive material including pores having diameters that approximate the size of the contaminants drawn from the lens is advantageous in that it lessens the likelihood that any contaminants can pass through the reactive material without being adsorbed onto the walls of the reactive material. A reactive material having pores ranging in size from 0.1 micron to 0.5 micron will adsorb on the surface and within the porous structure of the material contaminants having molecular weights of between 1 thousand to 1 million daltons.

The pores of the reactive material may be varied in shape in order to optimize the performance of the treatment apparatus. Materials having pore sizes that are tortuous, irregularly shaped and generally of long length advantageously have a larger surface area-to-volume ratio than materials with regular shaped, shallow pores. Moreover, the amount of active surface of the material in close proximity to the lens is increased, thereby increasing the likelihood of rapid adsorption of contaminants onto the surface of the reactive material.

The pores of the reactive layer may also be varied in distribution through the reactive layer to optimize the performance of the treatment apparatus. For example, a reactive layer may have pores of a larger size at or near the surface on which the lens is positioned. In this case, the contaminants that are generally of a larger size will be selectively retained near the surface while contaminants that are generally of a smaller size will be retained within the material at a depth away from the surface.

A further understanding of the invention can be obtained by reference to the following description of an evaluation conducted with respect to a conventional commercially available soft lens and the removal of compositions coated on the lens. This description is provided for purposes of illustration only and is not included to be limiting unless otherwise indicated.

Johnson & Johnson "ACUVUE" soft lenses were sectioned and immersed in test tubes containing artificial tear solution comprising 1.2 mg/ml egg white lysozyme, 3.9 mg/ml of bovine serum albumin, and 1.6 mg/ml of gamma globulin in a citric acid phosphate isotonic buffer solution. To ensure that each lens was coated with protein, the test tubes containing the lenses were shaken for 2 hours at room temperature. The sectioned lenses were removed and inspected. Generally, the lenses had a filmy appearance. Each of the lenses was placed in 2 milliliters of physiological saline solution and mixed for 10 seconds to remove any unbound protein. The rinsing step was repeated twice.

Each of the lenses was then individually positioned on a surface of reactive material. Specifically, the reactive material comprised a thin layer of PVDF moistened with a physiological saline solution. The lenses were allowed to remain positioned in contact with the material for various periods of time, after which each lens was removed from the material and inspected. Generally, the filmy appearance of the lens had decreased depending on the length of time the lens was allowed to remain in contact with the material.

To determine to what extent the contaminants had been removed from the lens by the reactive material, the reactive material was first allowed to air dry. Subsequently, the material was immersed in a staining solution of Commassie brilliant blue comprising 0.2% Commassie brilliant blue in 50% methanol and 10% acetic acid. Commassie brilliant blue stained those portions of the reactive material that had adsorbed protein. The reactive material was removed from the stain and washed with a solution comprising 22.5% methanol and 3.5% acetic acid to remove any stain not bound to compositions on the material. Each of the material sections showed a distinct blue staining generally corresponding to the outline of the corresponding sectioned lens.

A pair of lenses may be advantageously treated using the apparatus of the present invention as follows. First, the treatment apparatus 10 is removed from its wrapper 14 and the lens containers 11 and 12 are opened. Then, the lenses are removed and positioned on the pre-wetted reactive surfaces 25 and 36 of the two lens containers. The two lens containers are then closed, causing the optical surfaces of the lenses to be brought into contiguous wetted contact with the reactive surfaces of the apparatus. The lenses are allowed to remain in the closed containers for a period of time proportional to the degree to which the lenses are contaminated and/or the length of time since the lenses were last cleaned. Generally, a significant amount of contaminants are dislodged from contaminated-coated lenses that remain in the housing for a period of 2 hours. Heavily contaminated lenses may require a longer period of time, such as overnight when the wearer is sleeping.

After the treatment has been accomplished, the lenses are removed from the containers and returned to the user's eyes. The lens containers are closed, and the treatment apparatus, now containing the contaminants within its sealed containers, may be approximately disposed.

While embodiments of the apparatus discussed above include a reactive material layered over compressible material, an additional embodiment of the invention may provide wetted reactive material formed in a lens receiving shape without a housing or compressible layer to accommodate a lens on and/or between the material. The reactive material may itself close around the lens, or the reactive material may be held against the lens within the apparatus package or by means of external closing means. An additional embodiment of the apparatus may provide a reactive layer and wetted compressible layer without a housing, and external closing means around the compressible layer to maintain the reactive layer engaged to the lens. The package material may be formed, for example, of polymeric and/or paper with or without foil for protection, sealing and/or enhancing the identification of the apparatus.

While particular embodiments of the invention have been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. An apparatus for cleaning a contact lens having an optical surface and contaminated with contaminant matter, comprising:
   a layer of porous reactive material having a higher affinity for lipid contaminants relative to that of the lens defining a non-abrasive reactive surface operative when in wetted contact with the optical surface to attract lipid contaminant matter from the lens;
   said layer of reactive material being wetted with an opthalmologically compatible liquid;
   and a container for maintaining said reactive material in stationery contiguous wetted engagement with the optical surface.

2. A lens cleaning apparatus as defined in claim 1 wherein said reactive material has a higher physical affinity for lipid contaminants relative to that of the lens.

3. A lens cleaning apparatus as defined in claim 1 wherein said reactive material has a higher chemical affinity for lipid contaminants relative to that of the lens.

4. A lens cleaning apparatus as defined in claim 1 wherein said reactive material has a charged surface.

5. A lens cleaning apparatus as defined in claim 1 wherein said reactive material forms chemical linkages with said lipid contaminants.

6. A lens cleaning apparatus as defined in claim 1 wherein said reactive layer is selected from the group consisting of polytetrafluoroethylene, polyvynilidene fluoride, polypropylene, polyethylene, polyacrylonitrile, polymethylmethacrylate, polysulfone, polycarbonate, cellulose acetate, and polyamide reactive materials.

7. An apparatus for cleaning a contact lens having an optical surface and contaminated with contaminant matter, comprising:
   a layer of porous reactive material having a higher affinity for protein contaminants relative to that of the lens defining a non-abrasive reactive surface operative when in wetted contact with the optical surface to attract lipid contaminant matter from the lens;
   said layer of reactive material being wetted with an opthalmologically compatible liquid;
   and a container for maintaining said reactive material in stationery contiguous wetted engagement with the optical surface.

8. A lens cleaning apparatus as defined in claim 7 wherein said reactive material has a higher physical affinity for protein contaminants relative to that of the lens.

9. A lens cleaning apparatus as defined in claim 7 wherein said reactive material has a higher chemical affinity for protein contaminants relative to that of the lens.

10. A lens cleaning apparatus as defined in claim 7 wherein said reactive material has a charged surface.

11. A lens cleaning apparatus as defined in claim 7 wherein said reactive material forms chemical linkages with said protein contaminants.

12. A lens cleaning apparatus as defined in claim 7 wherein said reactive layer is selected from the group consisting of polytetrafluoroethylene, polyvynilidene fluoride, polypropylene, polyethylene, polyacrylonitrile, polymethylmethacrylate, polysulfone, polycarbonate, cellulose acetate, and polyamide reactive materials.

13. An apparatus for cleaning a contact lens having an optical surface and contaminated with contaminant matter, comprising:
   a layer of porous reactive material having a higher affinity for lipid and protein contaminants relative to that of the lens defining a non-abrasive reactive surface operative when in wetted contact with the optical surface to attract lipid and protein contaminant matter from the lens;
   said layer of reactive material being wetted with an opthalmologically compatible liquid;
   and a container for maintaining said reactive material in stationery contiguous wetted engagement with the optical surface.

14. A lens cleaning apparatus as defined in claim 13 wherein said reactive material has a higher physical affinity for lipid and protein contaminants relative to that of the lens.

15. A lens cleaning apparatus as defined in claim 13 wherein said reactive material has a higher chemical affinity for lipid and protein contaminants relative to that of the lens.

16. A lens cleaning apparatus as defined in claim 13 wherein said reactive material has a charged surface.

17. A lens cleaning apparatus as defined in claim 13 wherein said reactive material forms chemical linkages with said lipid and protein contaminants.

18. A lens cleaning apparatus as defined in claim 13 wherein said reactive layer is selected from the group consisting of polytetrafluoroethylene, polyvynilidene fluoride, polypropylene, polyethylene, polyacrylonitrile, polymethylmethacrylate, polysulfone, polycarbonate, cellulose acetate, and polyamide reactive materials.

* * * * *